(12) United States Patent
Groos et al.

(10) Patent No.: US 8,552,718 B2
(45) Date of Patent: Oct. 8, 2013

(54) METHOD FOR THE NONDESTRUCTIVE TESTING OF PIPES

(75) Inventors: Andreas Groos, Rheurdt (DE); Stefan Nitsche, Müheim (DE)

(73) Assignee: V & M Deutschland GmbH, Düsseldorf (DE)

( * ) Notice: Subject to any disclaimer, the term of this patent is extended or adjusted under 35 U.S.C. 154(b) by 194 days.

(21) Appl. No.: 12/992,710

(22) PCT Filed: Apr. 2, 2009

(86) PCT No.: PCT/DE2009/000448
§ 371 (c)(1),
(2), (4) Date: Feb. 2, 2011

(87) PCT Pub. No.: WO2009/138050
PCT Pub. Date: Nov. 19, 2009

(65) Prior Publication Data
US 2011/0268343 A1   Nov. 3, 2011

(30) Foreign Application Priority Data

May 15, 2008 (DE) .......................... 10 2008 024 394

(51) Int. Cl.
*G01N 27/82* (2006.01)
*G06K 9/00* (2006.01)
(52) U.S. Cl.
USPC ............ 324/237; 324/238; 324/240; 382/141
(58) Field of Classification Search
USPC ....................................... 324/237
See application file for complete search history.

(56) References Cited

U.S. PATENT DOCUMENTS 3,099,746 A * 7/1963 Walters ........................... 378/54
3,401,332 A * 9/1968 McClurg et al. ............... 324/227

(Continued)

FOREIGN PATENT DOCUMENTS

DE    102004035174     2/2006
EP      1 847 829 A1   10/2007

(Continued)

OTHER PUBLICATIONS

STIC Search Report, STIC Database Tracking No. 423674, To: Chris Mcandrew Location: Jeff 9 A 48, Date: Jun. 5, 2013 Case U.S. Appl. No. 12/992,710.*

(Continued)

*Primary Examiner* — Jermele M Hollington
*Assistant Examiner* — Christopher McAndrew
(74) *Attorney, Agent, or Firm* — Henry M. Feiereisen LLC

(57) ABSTRACT

In a method for the nondestructive testing of pipes made of ferromagnetic steel for flaws by means of stray flux, the pipe is magnetized by a constant field and the discontinuities in the near-surface region of the outer or inner surface of the pipe cause magnetic stray fluxes, which exit the pipe surface and are detected by probes of a test unit, wherein the association of the detected amplitude signals is performed on the basis of the amplitude height and/or the frequency spectrum with respect to an external or internal flaw via defined flaw thresholds respectively. For this, prior to associating the detected amplitude signals to an external or internal flaw, the angular position of the flaw relative to the respective magnetic field direction is determined, and a correction of the signals is carried out via a previously determined correction factor for amplitudes and/or frequencies of a perpendicular angular position.

4 Claims, 1 Drawing Sheet

(56) References Cited

U.S. PATENT DOCUMENTS

| | | | |
|---|---|---|---|
| 3,437,810 A * | 4/1969 | Walters et al. | 378/89 |
| 3,437,917 A * | 4/1969 | Gunkel et al. | 324/226 |
| 3,449,662 A * | 6/1969 | Wood | 324/220 |
| 3,462,602 A * | 8/1969 | Apple | 250/338.1 |
| 3,491,288 A * | 1/1970 | Forster | 324/213 |
| 3,538,433 A * | 11/1970 | Wood et al. | 324/227 |
| 3,906,357 A * | 9/1975 | Runshang | 324/226 |
| 4,117,403 A * | 9/1978 | Forster et al. | 324/240 |
| 4,247,818 A * | 1/1981 | Hiroshima et al. | 324/202 |
| 4,247,819 A * | 1/1981 | Shimada et al. | 324/233 |
| 4,439,730 A * | 3/1984 | Kauffman | 324/232 |
| 4,495,587 A * | 1/1985 | Plante et al. | 702/38 |
| 4,507,608 A * | 3/1985 | Flach et al. | 324/220 |
| 4,620,152 A * | 10/1986 | Bains, Jr. | 324/225 |
| 4,821,204 A * | 4/1989 | Huschelrath | 702/38 |
| 5,041,786 A * | 8/1991 | Takaishi et al. | 324/240 |
| 5,414,353 A * | 5/1995 | Weischedel | 324/232 |
| 5,476,010 A * | 12/1995 | Fleming et al. | 73/620 |
| 5,509,320 A * | 4/1996 | Forster | 73/866.5 |
| 5,534,775 A * | 7/1996 | Lam et al. | 324/216 |
| 5,793,205 A * | 8/1998 | Griffith et al. | 324/238 |
| 6,917,196 B2 * | 7/2005 | Kwun et al. | 324/240 |
| 6,966,816 B2 * | 11/2005 | Swedek et al. | 451/5 |
| 7,171,854 B2 * | 2/2007 | Nagashima et al. | 73/622 |
| 7,215,118 B2 * | 5/2007 | Park et al. | 324/238 |
| 7,389,706 B2 * | 6/2008 | Bratton et al. | 73/865.8 |
| 7,759,931 B2 * | 7/2010 | Tsukada et al. | 324/235 |
| 8,008,913 B2 * | 8/2011 | Qiao et al. | 324/225 |
| 8,104,349 B2 * | 1/2012 | Kubota et al. | 73/618 |
| 8,344,725 B2 * | 1/2013 | Fischer et al. | 324/238 |
| 8,368,395 B2 * | 2/2013 | Weischedel | 324/238 |
| 2001/0017540 A1 * | 8/2001 | Arai | 324/236 |
| 2006/0152216 A1 * | 7/2006 | Higuchi | 324/237 |
| 2008/0042645 A1 * | 2/2008 | Kaack et al. | 324/220 |
| 2008/0228412 A1 * | 9/2008 | Orth et al. | 702/38 |
| 2009/0059206 A1 * | 3/2009 | Churchill et al. | 356/72 |
| 2009/0250213 A1 * | 10/2009 | Kalb et al. | 166/255.1 |
| 2010/0102808 A1 * | 4/2010 | Boenisch | 324/240 |
| 2011/0268343 A1 * | 11/2011 | Groos et al. | 382/141 |

FOREIGN PATENT DOCUMENTS

| | | |
|---|---|---|
| JP | 62185162 A | 8/1987 |
| WO | WO 02/095383 A2 | 11/2002 |
| WO | WO 2006/007807 | 1/2006 |

OTHER PUBLICATIONS

Don E Bray et al.: "Nondestructive Evaluation. A tool in Design, Manufacturing, and Service", CRC Press, 1997.

* cited by examiner

METHOD FOR THE NONDESTRUCTIVE TESTING OF PIPES

CROSS-REFERENCES TO RELATED APPLICATIONS

This application is the U.S. National Stage of International Application No. PCT/DE2009/000448, filed Apr. 2, 2009, which designated the United States and has been published as International Publication No. WO 2009/138050 and which claims the priority of German Patent Application, Serial No. 10 2008 024 394.9, filed May 15, 2008, pursuant to 35 U.S.C. 119(a)-(d).

BACKGROUND OF THE INVENTION

The invention relates to a method for the nondestructive testing of pipes of ferromagnetic steel by means of stray flux.

The known stray flux test is used in pipes of ferromagnetic steel for detecting longitudinally aligned or transversally aligned near-surface discontinuities, like, e.g., cracks, that could otherwise not be detected at all or only with high inaccuracy when using other test methods in a cost-intensive and time-consuming manner.

This method detects e.g. cracks which extend from the surface of the pipe at least by about 0.3 mm (Nondestructive Evaluation, A Tool in Design, Manufacturing, and Service, CRC Press 1997).

Known prior art measuring methods for detection of near-surface flaws on the inner or outer sides of pipes involve the application of constant field magnetization.

In contrast to alternating field magnetization which is used, for example, in bar material and which permits only detection of external flaws of pipes, the constant field magnetization allows also detection of flaws on the inner surface of pipes.

The stray flux testing with constant field magnetization utilizes the effect that the induction flux density increases in the area of a flaw, whereby the magnetic field lines are disturbed by external or internal flaws in their otherwise straight expansion, thereby forming a so-called stray flux. This stray flux, which exits from the pipe surface, is used for the detection of flaws.

The magnetic stray flux is measured, e.g., with induction coils, Hall probes, or GMR sensors, which are arranged in a test head.

A magnetic field is applied at a right angle when testing for longitudinal flaws, and along the pipe axis when testing the pipe for longitudinal transverse flaws. The entire pipe surface is then inspected for flaws during the course of a continuous and quality-assuring pipe production.

In order to measure the entire surface during testing of the pipe for longitudinal flaws, it is necessary to move the pipe and test head relative to each other in a helical manner. This may be realized, e.g., by transporting and simultaneously rotating the pipe in a longitudinal direction under the fixedly arranged test head, or with a test head that orbits in a circular manner about the pipe while the pipe moves only in the longitudinal pipe direction, or by only rotating the pipe about a test head which is moveable in longitudinal pipe direction, or by moving the test head in a helical manner about the pipe while the pipe is at a standstill.

The test for transversal flaws typically involves a probe ring which is fixedly positioned about the pipe, with the pipe moving under the probe ring in longitudinal direction. When testing for a combination of longitudinal and transversal flaws, the movement patterns that are possible for testing for longitudinal flaws may also ensue.

The processed signals can then be used for sorting and marking the pipes and the test results can be recorded.

The test device is aligned by using a groove as test flaw which has been introduced onto a reference workpiece exactly in perpendicular relation to the testing or magnetic field direction. As soon as the test flaw is no longer perpendicular in relation to the magnetic field, the signal amplitude decreases progressively as the angle increases.

Although the known stray flux test is able to reliably detect possible discontinuities on the pipe surface, an association of the flaw signals to the outer and inner surfaces of the pipe, i.e. a separation of flaws when the flaws is oriented at an angle with respect to the magnetic field direction, is not possible with this method with sufficient certainty.

A separation of flaws according to outer or inner surface flaws on the pipe is desirable for many reasons even when flaws extend at an angle to the magnetic field. Flaws on the outer or inner surface of the pipe may have different origins, caused, for example, by the preceding production steps (defective internal tool or rollers) or by flaws in the source material.

Furthermore, an early fault localization and fault recognition with respective corrective measures may assist in the prevention of high failure and reworking rates. Depending on the pipe diameter, it may no longer be possible to rework flaws on the inner surface of the pipe, so that these pipes have to be sorted out as rejects at any rate.

According to experiments performed in-house, even a frequency analysis of the measured signals is not sufficient for an accurate association of flaws, since the measured frequencies are located close to one another and a type of "background noise" is additionally superimposed. This effectively coherent background signal may have various causes, e.g., wall thickness variations caused by rolling.

For this reason, according to WO 02/095383 A2, an attempt is made to minimize this background signal by forming a local difference between the measured signals obtained from at least two single probes located in the same plane.

For comparable flaw dimensions, the amplitudes and frequencies of the stray fluxes on the pipe outer surface caused by internal flaws are in general markedly lower than those that are produced by flaws on the outer surface of the pipe. Therefore, the sensitivity of the probes to possible internal flaws is used in the known stray flux method to attain a reliable recognition of flaws.

However, this principle fails as soon as a flaw is no longer traversed in perpendicular relation to the test or magnetic field direction so that, as a result of the lower frequency spectrum, this flaw is either no longer detected with certainty because, e.g., the frequency spectrum is only insignificantly lower compared to that of an external flaw, or is classified by mistake as internal flaw and tested in relation to the more sensitive internal flaw threshold.

This has the added disadvantage that external flaws, which may still be tolerated, are detected with too high sensitivity and may then be indicated as no longer tolerable internal flaws, resulting in unnecessary rejection or redundant reworking of the pipes.

JP 62185162A discloses detection of the angular position or shape of a flaw extending from a workpiece surface into the interior by means of stray flux technique. Amplitude signals are here generally detected by two spaced-apart sensors placed perpendicular, evaluated, related to one another, wherein an indication of the shape or angular position of the flaw is derived from the relationship. This document provides no indication as to an evaluation of flaw signals extending at an angle with respect to the test or magnetic field direction and as to how a separation of external and internal flaws can be achieved.

SUMMARY OF THE INVENTION

It is an object of the invention to provide a reliable and cost-effective method for the nondestructive testing of pipes of ferromagnetic steel by means of a stray flux, with which the fault recognition can be made more reliable even when flaws are involved which extend at an angle with respect to the pipe axis, and with which an unambiguous association of flaws to the outer or inner surface of the pipe becomes possible.

According to the invention, this object is attained by determining the angular position of the flaw in relation to the magnetic field direction before associating the detected amplitude signals to an external or internal flaw, and by correcting the signals via a correction factor determined beforehand for amplitudes and/or frequencies of a vertical angular position.

The method according to the invention is based on the observation that at known angular position of the flaw in relation to the direction of the respective magnetic field for the testing of longitudinal or transversal flaws in the pipe, the amplitude height and/or signal frequency in relation to a respective vertical angular position (reference position) can be corrected using previously determined correction factors. As a result, the classification as external or internal flaw may optionally be modified, leading advantageously to a decrease in rejects and in reworking of presumably defective pipes.

Depending on the intended task of the test, either only the amplitude height or the frequency may be corrected, although optionally both measuring variables can be corrected.

A core of the proposed solution is the determination of a flaw angle in relation to the scanning direction or magnetic field direction.

The test flaw, used for adjusting the device, is typically introduced perpendicular to the scanning direction. The amplitude and frequency of the flaw as measured by the testing probe when passing over the flaw for internal and external test flaws, respectively, is used for adjusting the flaw thresholds and filters.

As soon as a flaw is no longer oriented perpendicular to the scanning direction, the amplitude and frequency of the flaw changes so that respective corrective values can be ascertained therefrom.

The method according to the invention thus permits to provide the measured amplitudes and/or frequencies with respective correction factors when the flaw angle is known, and to realize a correct association of the flaw.

Furthermore, the method improves also the detection of angled external flaws which heretofore could not be detected or could only be detected in a difficult manner and which have a frequency spectrum that is only insignificantly smaller compared to an external flaw extending perpendicular (and which thus cannot be detected via the lower internal flaw threshold) as well as in particular of angled internal flaws.

In general, emphasis is placed on the capability of the method to detect also angled flaws with the same sensitivity as flaws extending perpendicular to the magnetic field.

The flaw angle can be determined in accordance with a first method variation for example through examination of the amplitude/time representations of several probes arranged side-by-side, the so-called A-images. A threshold, either a sliding threshold that conforms to the background, or a fixed threshold that adapts itself to the display height of the test flaw, is placed across each of the probe channels. A further signal filtering may optionally take place beforehand to lower the level of the background noise. As soon as the measuring signal of a probe exceeds this threshold, the measuring signals of the neighboring probes are also examined for indication above the threshold.

Optionally, the required display height may even be smaller in the neighboring channels than the threshold utilized for triggering the evaluation.

When elongated flaws are detected by several neighboring probes, the localized maximum amplitude as well as the time between the indicated signals is stored.

The flaw angle or the flaw curvature can be calculated by converting/associating the time to the location and thereafter adapting a compensating straight line or compensating curve through the amplitude maxima.

As an alternative to the afore-described method, a second variation of the method involves a determination of the flaw angle from a representation in which the flaw amplitudes are plotted over the specimen surface (flaw C-image), e.g. though use of image processing algorithms.

This enables
 correction of the flaw amplitude e.g. via a previously measured comparison of the amplitude of grooves that are traversed perpendicularly and at an angle, and
 to correct, based on the flaw angle/flaw curvature, the classification as internal or external flaw.

BRIEF DESCRIPTION OF THE DRAWING

The invention will now be described in greater detail with reference to the figures. Identical reference signs in different figures designate identical components. It is shown in.

DETAILED DESCRIPTION OF PREFERRED EMBODIMENTS

Figure 1:
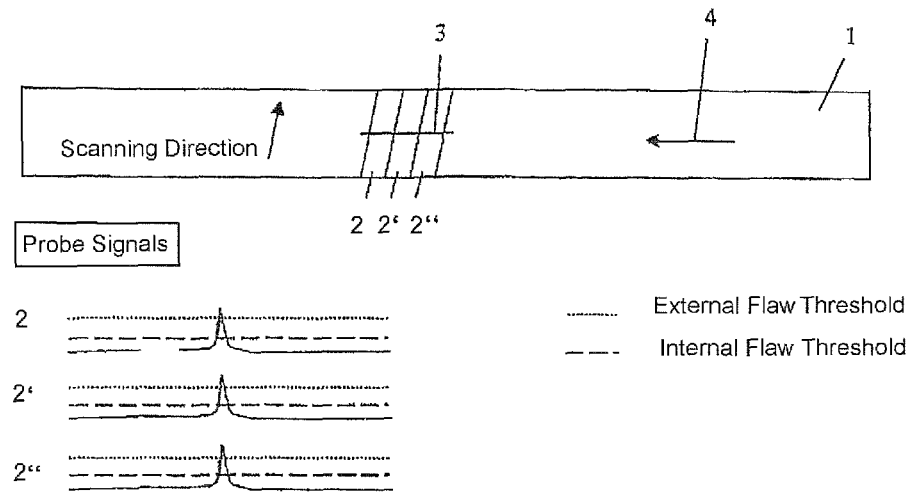
FIG. 1 a schematic illustration of a method variation according to the invention with amplitude correction of stray flux signals for flaws extending along the pipe axis, FIG. 2 like FIG. 1, but with flaws extending at an angle with respect to the pipe axis.

FIG. 1 shows schematically in the upper part a pipe 1 to be tested, which has on the pipe outer surface a flaw 3 oriented longitudinally in relation to the pipe axis (longitudinal flaw). The test unit is here configured for a test for longitudinal flaws, i.e. the magnetic field of the magnetization yoke, not shown here, is aligned perpendicular to the pipe axis.

The test unit includes three test probes 2, 2', 2" of a straight probe which includes (not shown) induction coils arranged for rotation about the pipe and disposed in a plane parallel next to one another in axial direction of the pipe.

As indicated by arrow 4, when testing for longitudinal flaws the pipe 1 is moved in the longitudinal direction and the test unit is simultaneously rotated so that the entire pipe surface is scanned in helical manner in the scanning direction indicated by the arrow.

The time sequence of the probe signals of the individual probes 2, 2', and 2", as detected by the test unit, is illustrated in the lower part of FIG. 1.

Likewise, when the flaw 3 on the pipe outer surface is oriented longitudinally in relation to the pipe axis and the scanning direction and perpendicular to the magnetic field, the flaw 3 is detected by the three probes 2, 2', 2" at the same time and displayed correctly as external flaw, commensurate with the flaw thresholds defined for differentiating between external and internal flaws, based on the frequency spectrum/ amplitude height.

Figure 2:
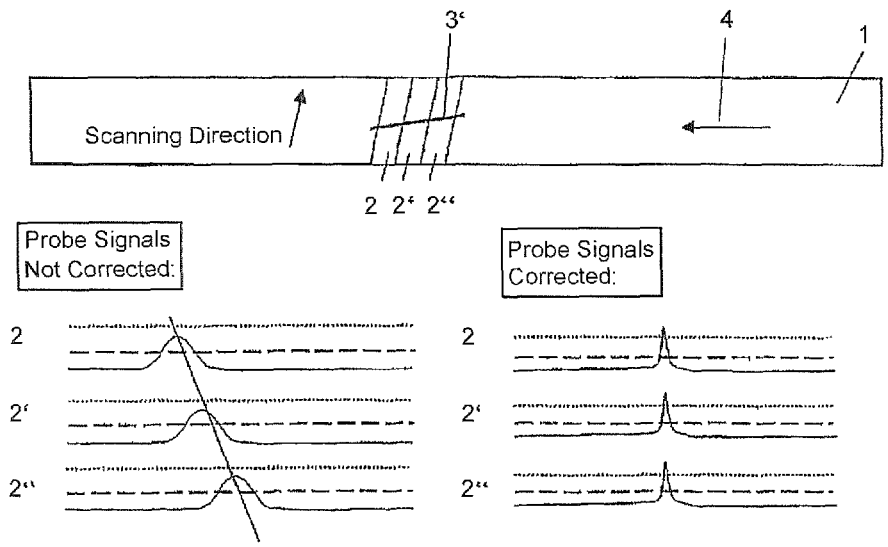

FIG. 2 shows the chronological signal sequence of the three probes 2, 2', 2" in the event of an external flaw 3' extending at an angle in relation to the pipe axis or magnetic field direction. Test configuration and reference numerals in the upper part of FIG. 2 correspond, except for the angled flaws 3', to FIG. 1 so that a detailed description is not necessary.

In this case, the probes 2, 2', 2" detect the angled flaw 3', as depicted in the lower left part of FIG. 2, with a time offset, with the signals having a lower frequency spectrum and a lower amplitude height in view of the fact that the flaw is no longer oriented perpendicular to the magnetic field of the induction coils.

In view of the defined flaw thresholds for external and internal flaws, the angled external flaw is classified as internal flaw and thus associated incorrectly.

The method according to the invention provides now a correction of the determined signal amplitudes and the frequency spectrum. The locally maximal amplitude of the respective test probes 2, 2', 2" as well as also the time between the displayed signals is initially stored. Through conversion/association of the time to the location and subsequent adjustment of a compensation straight line or curve by the maxima, a flaw angle can be calculated, when the relative speed between pipe surface and test unit is known, and the measured amplitudes and frequencies can then be corrected via a previously determined correction factor for amplitudes and frequencies of a perpendicular angular orientation.

The amplitudes and frequencies corrected with the correction factor are illustrated in the lower right part of FIG. 2. As a result of the correction, the amplitudes and frequencies are now so depicted as if the flaw 3' were detected perpendicular to the magnetic field of the induction coils. The corrected amplitudes and frequencies thus correspond to the signals described in FIG. 1 and classify the angled flaw 3' correctly as external flaw, corresponding to the exceeded threshold value herefore.

The invention claimed is:

1. A method for the nondestructive testing of pipes of ferromagnetic steel for flaws by means of stray flux, comprising the steps of:
    magnetizing the pipe with a constant magnetic field having a direction,
    detecting with probes of a test unit for longitudinal and/or transversal flaw testing, amplitudes or frequencies or both of magnetic stray fluxes caused by a test flaw oriented perpendicular relative to the magnetic field direction;
    determining a correction factor as a function of the amplitudes or frequencies or both of the magnetic stray fluxes caused by the test flaw;
    determining an angular orientation of another flaw relative to the magnetic field direction;
    determining amplitudes or frequencies, or both, of magnetic stray fluxes caused by the other flaw,
    correcting the amplitudes or frequencies, or both, of the magnetic stray fluxes caused by the other flaw with the determined correction factor, and
    associating the corrected amplitudes or frequencies, or both of the magnetic stray fluxes with an external or internal flaw based on an amplitude height or a frequency spectrum, or both, via defined flaw thresholds.

2. The method of claim 1, wherein the angular position of the flaw is determined by:
    measuring maximum local amplitudes of at least two probes of the test unit arranged in the same plane in fixed spaced-apart relationship,
    measuring a time between the detected amplitude signals, and
    measuring a relative speed between pipe surface and the test unit, and
    relating the maximum local amplitudes, the time and the relative speed to one another.

3. The method of claim 1, wherein the angular orientation of the flaw is determined based on an optical image and an evaluation of the detected amplitude signals across the test surface.

4. The method of claim 1, wherein the angular orientation of the flaw is determined based on an optical image and wherein the optical image is processed via automated image processing.

* * * * *